US012685792B2

(12) United States Patent
Wallace et al.

(10) Patent No.: US 12,685,792 B2
(45) Date of Patent: Jul. 21, 2026

(54) CONNECTION SYSTEM AND ACTIVE STERILIZER FOR A DRUG DELIVERY DEVICE

(71) Applicant: West Pharmaceutical Services, Inc., Exton, PA (US)

(72) Inventors: Zachary Wallace, Philadelphia, PA (US); Lawton Laurence, Chester Springs, PA (US); Menaka Abeygunawardena, Blue Bell, PA (US); Eleftherios Hristofas, Lancaster, PA (US); John Basista, Ambler, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 1080 days.

(21) Appl. No.: 17/694,457

(22) Filed: Mar. 14, 2022

(65) Prior Publication Data

US 2022/0288248 A1      Sep. 15, 2022

Related U.S. Application Data

(60) Provisional application No. 63/160,871, filed on Mar. 14, 2021.

(51) Int. Cl.
| | |
|---|---|
| *A61L 2/04* | (2006.01) |
| *A61L 2/26* | (2006.01) |

(Continued)

(52) U.S. Cl.
CPC ................... *A61L 2/04* (2013.01); *A61L 2/26* (2013.01); *A61M 5/001* (2013.01); *A61M 5/162* (2013.01);

(Continued)

(58) Field of Classification Search
CPC ......... A61L 2/04; A61M 39/04; A61M 39/14; B29C 65/2046; B29C 65/20
See application file for complete search history.

(56) References Cited

U.S. PATENT DOCUMENTS 4,022,205 A * 5/1977 Tenczar .................. F16L 37/30
                                                                    285/21.2
4,619,642 A * 10/1986 Spencer .............. B29C 65/7841
                                                                    604/905

(Continued)

FOREIGN PATENT DOCUMENTS

WO      2008005882 A2      1/2008

OTHER PUBLICATIONS

Int'l Search Report and Written Opinion dated Sep. 22, 2022, issued in PCT/US2022/020192.

*Primary Examiner* — Maris R Kessel
*Assistant Examiner* — Eric Talbert
(74) *Attorney, Agent, or Firm* — Blank Rome LLP

(57) ABSTRACT

A method for creating an aseptic connection includes arranging a heating element between a first outer sealing surface and a second outer sealing surface such that the heating element is in contact with the first outer sealing surface and the second outer sealing surface. The method further includes applying opposing forces to the first and second outer sealing surfaces such that the first and second outer sealing surfaces are biased towards each other and heating the heating element to sterilize the first outer sealing surface and second outer sealing surface. The method also includes removing the heating element from between the first seal and second seal while continuing to apply the opposing forces to the first and second outer sealing surfaces such that the aseptic connection is simultaneously formed between the first and second outer sealing surfaces.

18 Claims, 8 Drawing Sheets

(51) Int. Cl.

| | |
|---|---|
| *A61L 103/00* | (2026.01) |
| *A61L 103/15* | (2026.01) |
| *A61M 5/00* | (2006.01) |
| *A61M 5/162* | (2006.01) |
| *A61M 5/44* | (2006.01) |
| *A61M 39/14* | (2006.01) |

(52) U.S. Cl.
    CPC ............ *A61M 5/44* (2013.01); *A61L 2103/15*
            (2026.01); *A61L 2103/23* (2026.01); *A61L*
            *2202/18* (2013.01); *A61M 39/14* (2013.01)

(56)                   References Cited

U.S. PATENT DOCUMENTS

| | | | |
|---|---|---|---|
| 2008/0009833 A1* | 1/2008 | Corbin ............... | B29C 65/2046 |
| | | | 604/533 |
| 2012/0204990 A1 | 8/2012 | Min | |
| 2018/0028747 A1* | 2/2018 | Hanson ................ | A61M 5/162 |
| 2019/0134295 A1 | 5/2019 | Plaskin | |
| 2021/0001048 A1* | 1/2021 | Schrul ................ | A61M 5/2466 |

\* cited by examiner

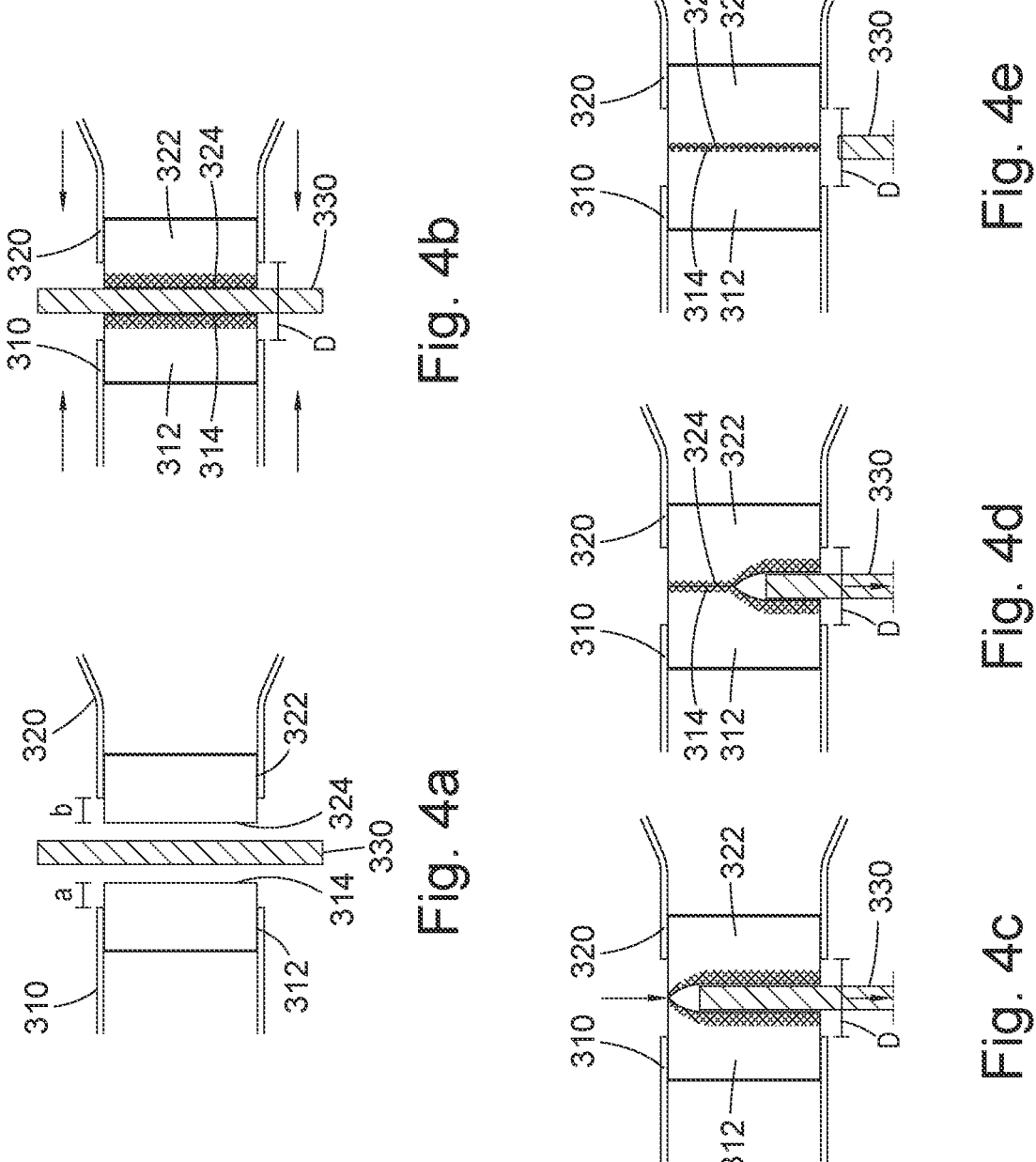

CONNECTION SYSTEM AND ACTIVE STERILIZER FOR A DRUG DELIVERY DEVICE

CROSS REFERENCE TO RELATED APPLICATIONS

This application claims the benefit of U.S. Provisional Patent App. No. 63/160,871, filed Mar. 14, 2021, the disclosure of which is hereby incorporated by reference herein.

FIELD

The present disclosure relates to a method and system for creating an aseptic connection between a first body and a second body, with particular application to drug delivery systems.

BACKGROUND

Injection devices, such as syringes and autoinjectors, deliver medicaments from a medicament container through a hypodermic needle. Because the hypodermic needle delivers medicaments to a patient's body, sterility of injection devices and medicament containers is of utmost importance.

Often, injection devices are manufactured and sold separately from medicament containers. As a result, a single injection device can be used to deliver a wide range of treatments, by connecting the injection device to a medicament container containing a medicament type and dosage for any one of the wide range of treatments. Before use, a manufacturer or a user (which can be a medical professional or patient) couples a medicament container containing a type and dose of medicament for the treatment required, to the injection device. A fluid connection is formed between the container and the hypodermic needle of the injection device, such that injection of the medicament can be performed. Collectively, the injection device and the container form an injection system.

In many injection systems, the container is initially sealed by a septum, thereby sealing the medicament within the container and maintaining sterility of the medicament. Furthermore, the injection device includes a transfer needle (separate from the hypodermic needle), the transfer needle being configured to pierce the septum once the container and the injection device are connected. A fluid conduit fluidly connects the transfer needle to the hypodermic needle. Therefore, once the transfer needle has pierced the septum, the medicament can be delivered to a patient through the hypodermic needle. Such injection systems are particularly useful for home use, because the connection between the container and the injection device is easy to achieve (by simply pushing the container or transfer needle into place). Such injection systems can also be used in hospitals or other clinical settings.

However, a problem exists that sterility of the outer surface of the septum, and of the transfer needle, is difficult to ensure. Accordingly, there is a risk that one or both of the outer surface of the septum and the transfer needle become contaminated, and that this contamination could enter the patient when an injection is formed. This risk is exaggerated where injection systems are used in the home, or settings in which a medical professional does not operate the injection system. Furthermore, a user may keep an injection device and containers in a non-sterile environment in the home, such as a drawer or cupboard, where contamination is likely.

SUMMARY

According to a first aspect of this disclosure, a method for creating an aseptic connection includes providing a first body defining an opening. A first seal seals the opening of the first body and the first seal defines a first outer sealing surface. The method includes providing a second body defining an opening. The second seal seals the opening of the second body and the second seal defines a second outer sealing surface. The method includes arranging the first outer sealing surface in an opposing relationship with the second outer sealing surface and arranging a heating element between the first outer sealing surface and the second outer sealing surface such that the heating element is in contact with the first outer sealing surface and the second outer sealing surface. The method includes applying opposing forces to the first and second outer sealing surfaces such that the first and second outer sealing surfaces are biased towards each other. The method includes heating the heating element to a predetermined temperature for a predetermined period of time to sterilize the first outer sealing surface and second outer sealing surface and removing the heating element from between the first seal and second seal while continuing to apply the opposing forces to the first and second outer sealing surfaces such that the aseptic connection is simultaneously formed between the first and second outer sealing surfaces.

Implementations of the first aspect can include the heating element defining a strip of electrically conductive material. The heating element can define a strip of thermally conductive material. The heating element can be heated by electrical resistance. The heating element can be heated by induction. The method can include securing the first outer sealing surface in a contacting relationship with the second outer sealing surface. A first engagement body and a second engagement body can respectively secure the first body and the second body in the opposing relationship and apply the opposing forces. In the opposing relationship a slot can be formed between the first outer sealing surface and the second outer sealing surface. The method can include securing the first engagement body and second engagement bodies to each other with the heating element arranged in the slot between the first outer sealing surface and second outer sealing surface and removing the heating element through the slot. The removing of the heating element from between the first seal and the second seal takes place after the step of securing the first engagement body and second engagement body. The first body defines a medicament container with a septum and the first seal seals the medicament container. The second body defines an enclosure in which a tip of a transfer needle is disposed and the second seal seals the enclosure. Arranging the heating element between the first outer sealing surface and second outer sealing surface can include inserting the heating element into a space between the first outer sealing surface and second outer sealing surface and advancing one or both of the first outer sealing surface and second outer sealing surface towards the heating element to a position in which the first outer sealing surface and second outer sealing surface contact the heating element. The first and second bodies can each be each empty, or one of the first and second bodies can contain a medicament. A method of assembling a drug delivery device can include creating an aseptic connection according to the one aspect of the disclosure between two components of the drug delivery device.

A second aspect of the disclosure includes a system for creating an aseptic connection. The system can include a first body and a first seal that seals the first body where the first seal defines a first outer seal surface. The system can include a second bod and a second seal that the seals the second body where the second seal defines a second outer seal surface. The system can include a first engagement body and a second engagement body that are configured to respectively secure the first body and the second body in an opposing relationship in which the first outer seal surface and the second outer seal surface contact each other. The system can include a heating element that is configured to extend between the first outer seal surface and the second outer seal surface while the first engagement body and the second engagement body are in the opposing relationship to interrupt contact between the first outer seal surface and the second outer seal surface and to sterilize the first outer seal surface and the second outer seal surface. The first engagement body and the second engagement body can respectively secure the first body and the second body in the opposing relationship such that contact between the first outer sealing surface and the second outer sealing is simultaneously restored upon removal of the heating element to provide the aseptic connection between the first outer sealing surface and the second outer sealing surface.

Implementations of the second aspect can include the first body defining a medicament container with a septum, and the second body defining an enclosure in which a tip of a transfer needle is disposed. The first and second bodies can each be empty, or one of the first and second bodies can contain a medicament. The heating element can be configured to heat the first and second outer sealing surfaces to temperatures exceeding 200° C. for at least 15 seconds.

BRIEF DESCRIPTION OF THE DRAWINGS

The invention will be described in more detail with reference to a number of non-limiting examples as shown in the following drawings, in which:

FIG. 2b shows a cutaway view of the injection system of FIG. 2a;

FIGS. 4a-4e show details of the connection system of FIG. 3a, showing a process of forming a sterile connection;

Like reference numerals are used for like components throughout the drawings.

DETAILED DESCRIPTION

Figure 1:
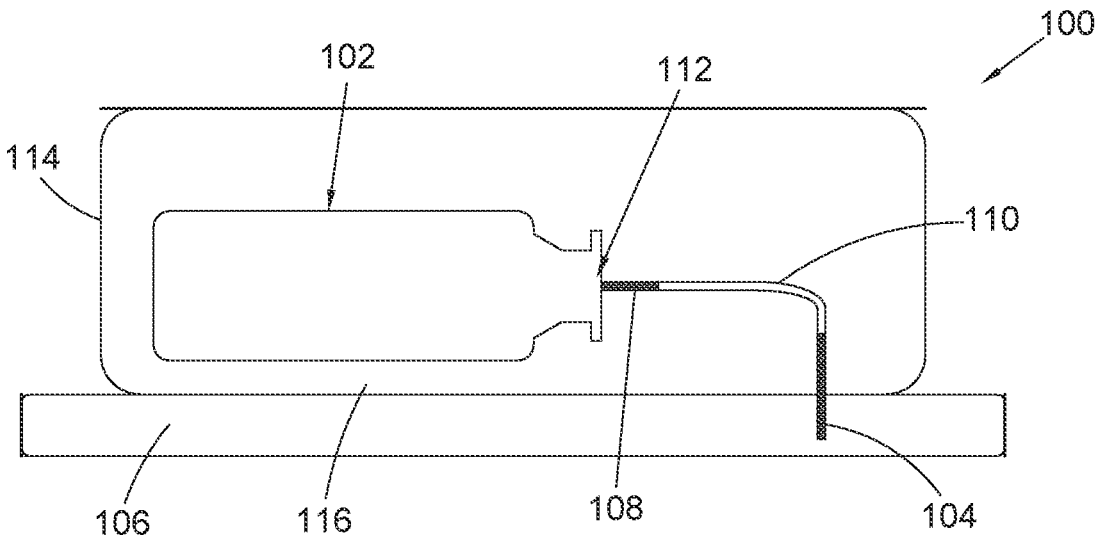
FIG. 1 shows a schematic illustration of an injection device.

FIG. 1 shows a schematic of an injection system comprising on-body injection device 100 and a medicament container 102. The injection system is shown in the assembled state, in which the medicament container 102 is coupled with the injection device 100 and the injection device 100 is ready for performing an injection.

As shown, the injection device 100 can include a hypodermic needle 104 for piercing the skin 106 of a patient and a transfer needle 108 that can be fluidly connected to the hypodermic needle 104 via a fluid conduit 110. As shown in the assembled state of FIG. 1, a free end of the transfer needle 108 can pierce a septum 112 of the medicament container 102. Accordingly, the hypodermic needle 104 can be in fluid communication with the medicament container 102 via the transfer needle 108 and the fluid conduit 110, such that a medicament from the medicament container 102 can be dispensed through the hypodermic needle 104.

The injection device 100 can include a housing 114, which can encase the components of the injection device 100 and can further encases the medicament container 102 when the injection system is in the assembled state, as shown in FIG. 1. The housing 114 can include a skin contact surface 116. The skin contact surface 116 can include an adhesive layer for secure attachment to a patient's skin.

The hypodermic needle 104 can translate relative to the housing 114 between a retracted position in which the hypodermic needle 104 is concealed within the housing 114, and an injection position (as shown in FIG. 1) in which the hypodermic needle 104 protrudes through an opening in the skin contact surface of the housing. Because the hypodermic needle 104 can be concealed within the housing 114 in the retracted state, risk of injury from the hypodermic needle 104 can be reduced or eliminated. In embodiments, the injection device 100 can be configured such that the hypodermic needle 104 only moves into the injection position once the injection device 100 has been secured to a patient's skin 106. In embodiments, injection device 100 can include a button and/or an actuator. The button and/or actuator can be provided on and/or within the housing 114 and can initiate an injection procedure. The actuator can be a mechanical actuator that can advance the needle into the injection site. In embodiments, the injection device 100 can include a control unit that can initiate an injection procedure (e.g., via the button and/or actuator).

In embodiments, the hypodermic needle 104 can be part of an infusion set that can be spaced from the housing 114, rather than being directly attached to the housing. In such embodiments, the injection device 100 can pump the medicament to the remotely located hypodermic needle for delivery to a patient.

Figure 2A:
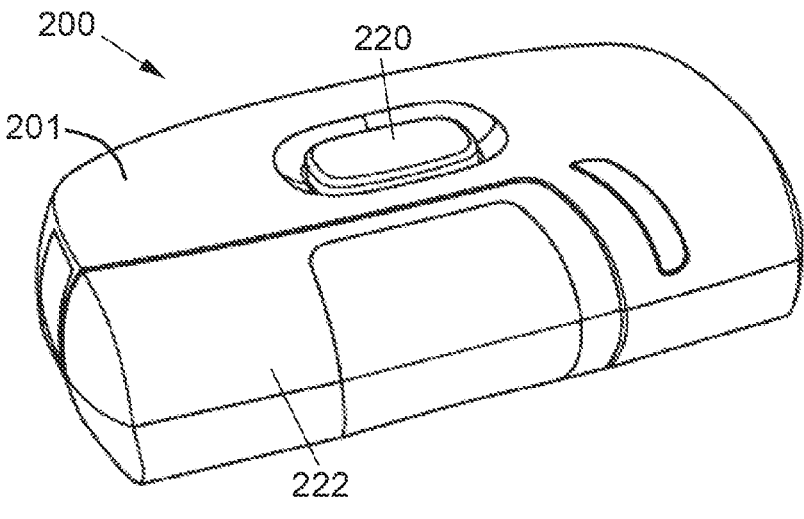
FIG. 2a shows an example injection system corresponding to FIG. 1.
Figure 2B:
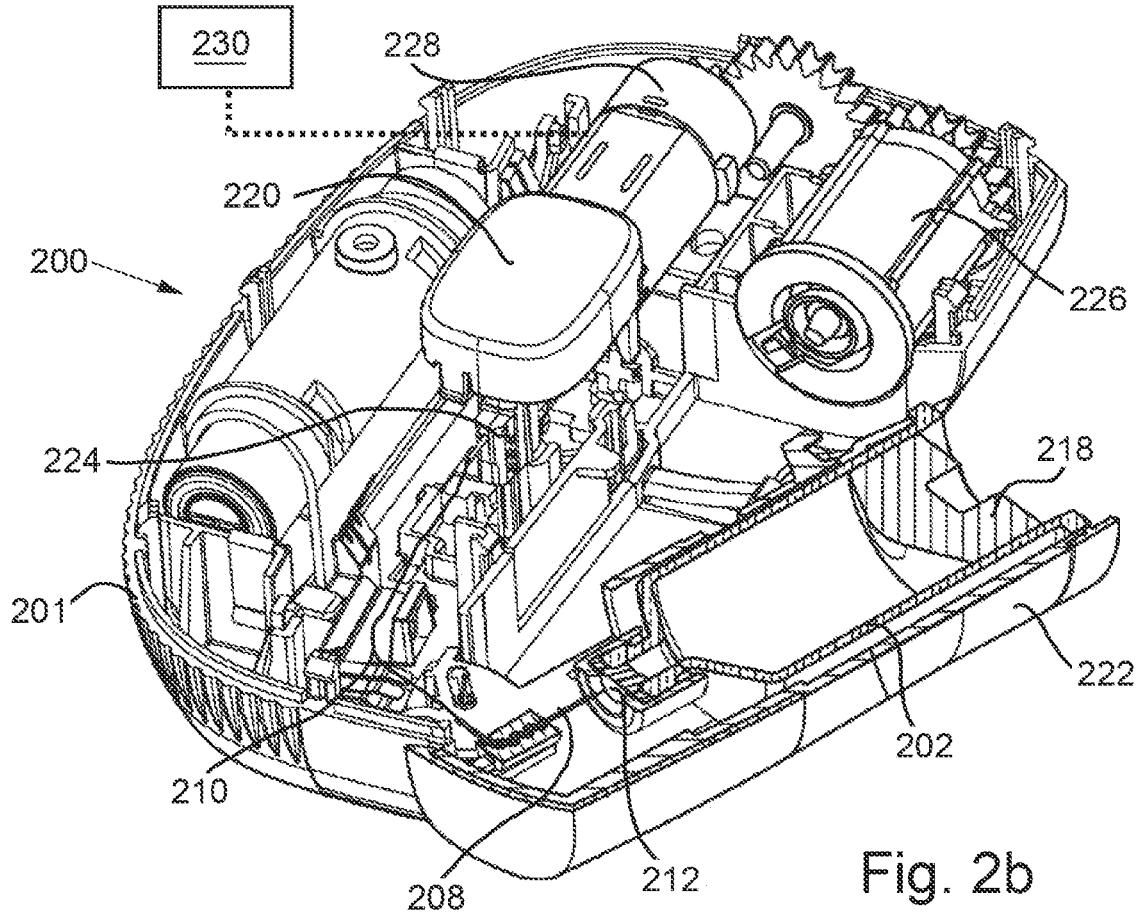

FIGS. 2a and 2b show an example wearable injection system 200. Unless indicated otherwise expressly or clearly by context, the injection system 200 can include any of the features of the injection device 100 and vice versa. FIG. 2a shows the injection system 200 in an assembled state ready for attachment to an injection site. The injection system 200 can include a housing 201 and an actuator button 220. The injection system 200 can also include a door 222 or hatch into which a medicament container 202 can be inserted. The door 222 can move between a closed position, as shown in FIG. 2a, and an open position, as shown in FIG. 2b. The injection system 200 and the medicament container 202 can be manufactured and/or sold separately and may be coupled to one another by a user or healthcare professional before use. The door 222 can allow access to an enclosure for receiving the medicament container 202. The enclosure can be accessible when the door 222 is in the open position and can secure the medicament container 202 within the housing 201 when the door 222 is in the closed position. Therefore, the medicament container 202 can be inserted into the enclosure of the injection system 200 when the door is in the open position.

As can also be seen from FIG. 2b, the medicament container 202 can include a septum 212 at a first end and a plunger 218 at a second end. The plunger 218 can move through the medicament container 202 from the second end and towards the first end. The plunger 218 can form a seal with the medicament container 202 to define an internal volume of the medicament container 202 that can contain a medicament. Movement of the plunger 218 towards the first end can reduce the internal volume of the medicament container 202, thereby applying pressure to and thus expelling the medicament from the medicament container 202 through a transfer needle 208 piercing the septum 212 at the first end of the medicament container 202.

As shown in FIG. 2b, the injection system 200 can include an insertion mechanism 224 that can advance the injection needle from a pre-injection position (within the housing 201) to an injection-ready position (as shown in FIG. 1). The injection system 200 can include a fluid conduit 210 that can connect the transfer needle 208 to the injection needle.

The injection system 200 can include a drive assembly that can advance the plunger 218 along the body of the medicament container 202. The drive assembly can include a telescopic screw assembly (TSA) 226 that can advance a piston rod. The injection system 200 can include a motor 228 that can drive the TSA 226 to advance the piston rod. The injection system 200 can include a control unit 230 (shown schematically in FIG. 2b) that can control actuation of the motor 228. The piston rod can engage the plunger 218 to advance the plunger 218 through the medicament container 202.

In the configuration shown in FIG. 2b, fluid communication between the transfer needle 208 and the internal volume of the medicament container 202 is prevented since the septum 212 (or other seal) has not yet been pierced by the transfer needle 208. However, before an injection can take place via the injection needle the transfer needle 208 must be brought into fluid communication with the internal volume of the medicament container 202. Sterility of the fluid conduit 210, the transfer needle 208, and the septum 212 can be maintained throughout this process.

Figure 3A:
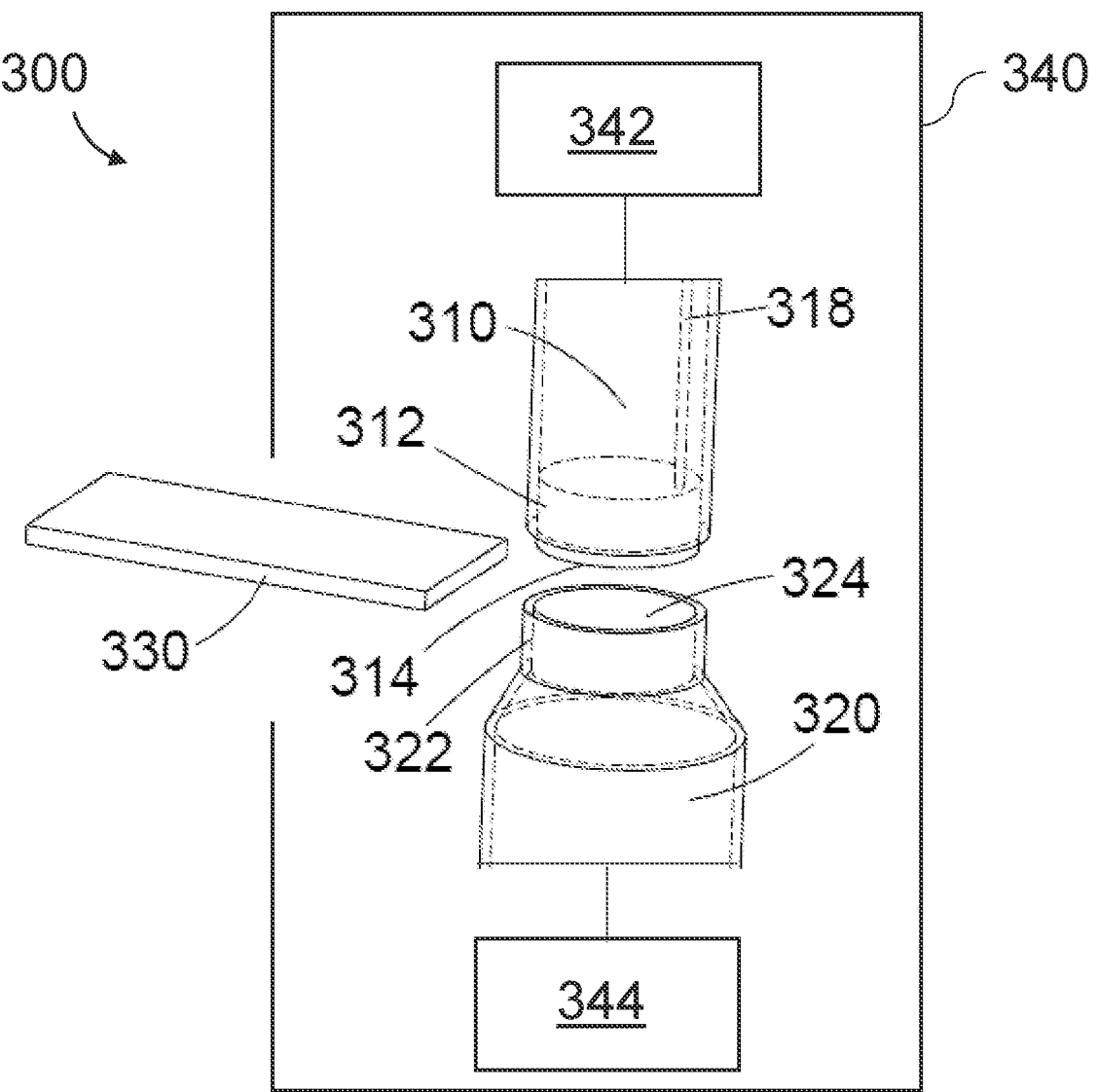
FIG. 3a shows a connection system according to the present disclosure, in an unconnected state.
Figure 3B:
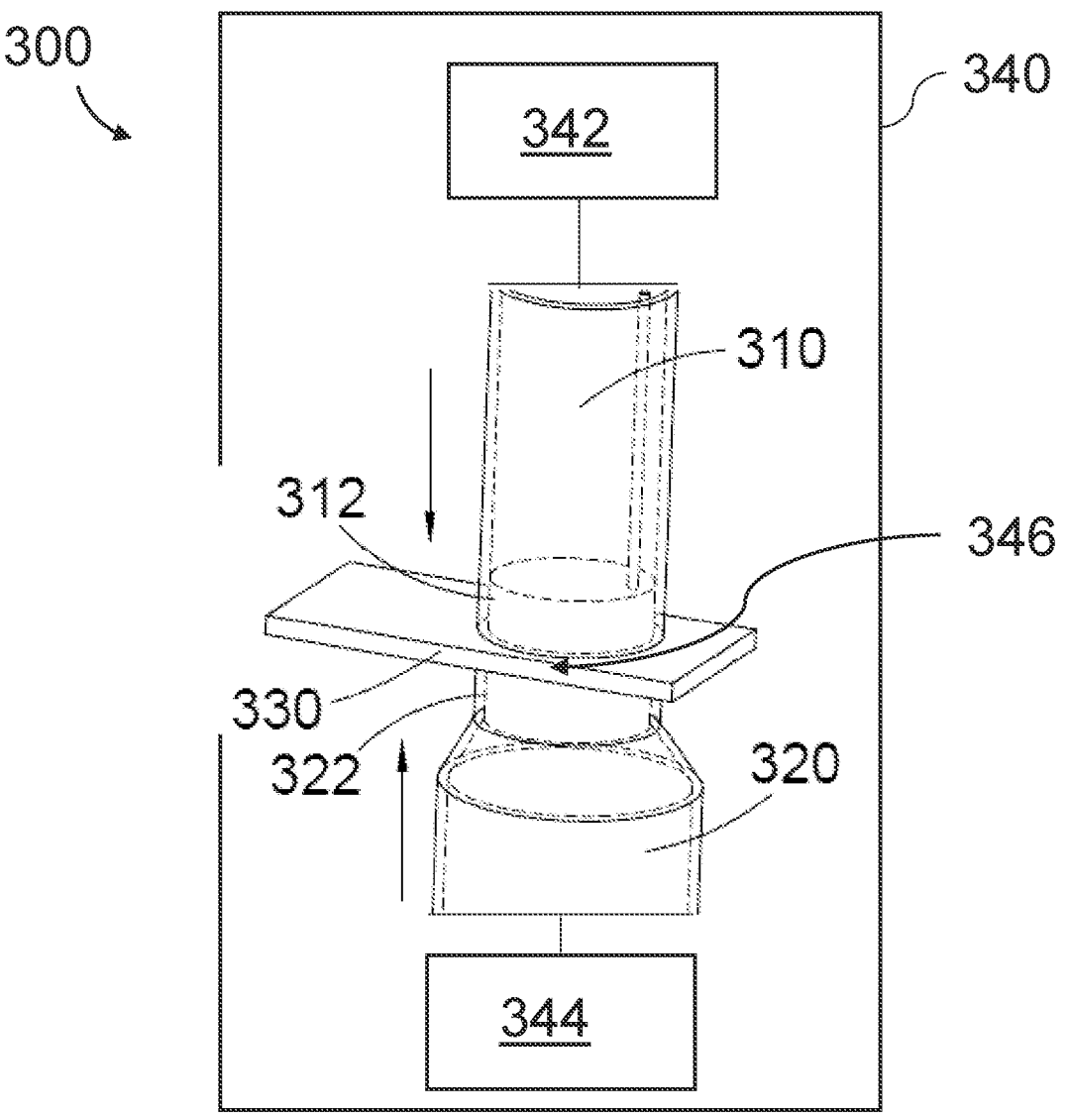
FIG. 3b shows the connection system of FIG. 3a in a first connected state.
Figure 3C:
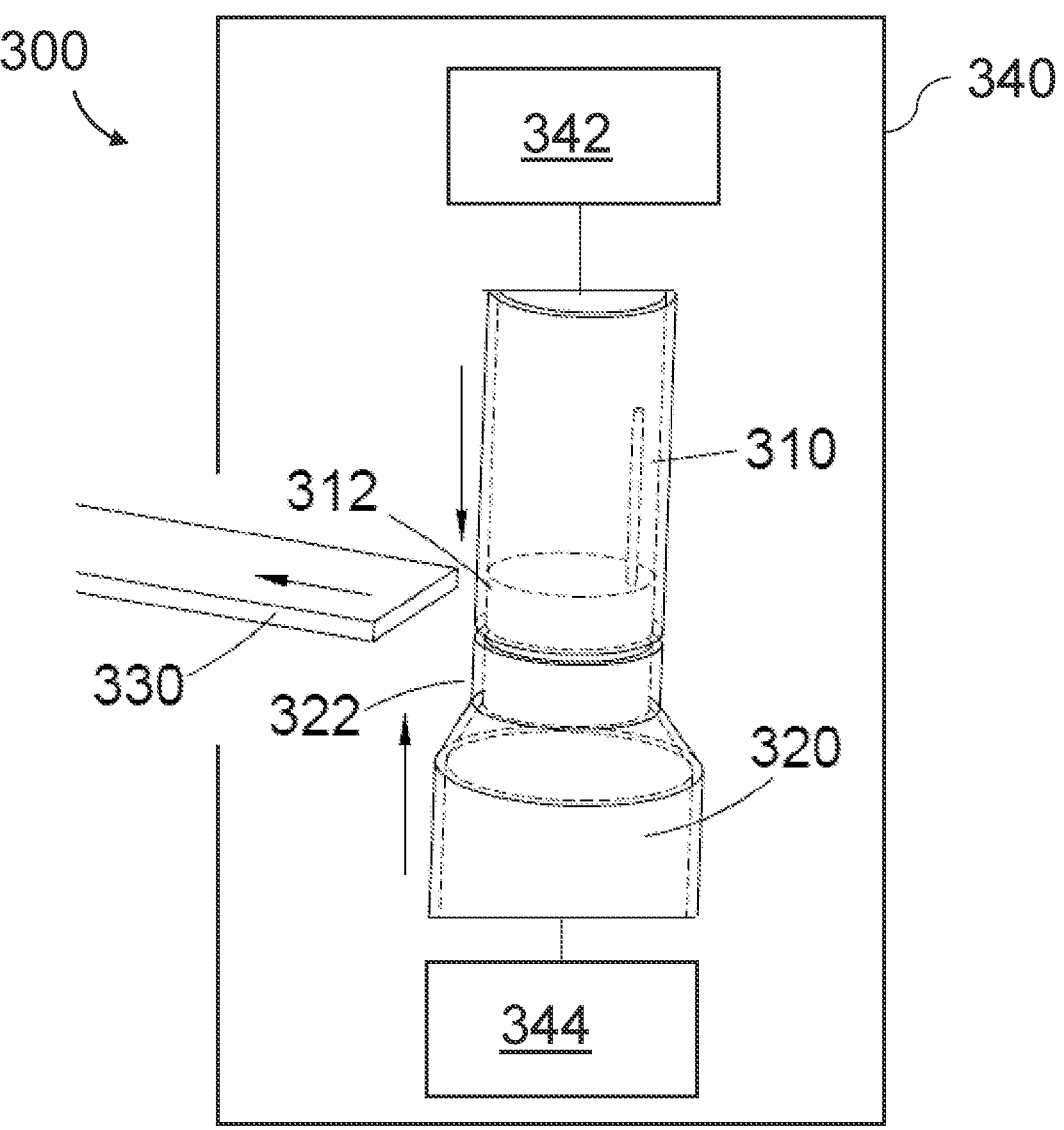
FIG. 3c shows the connection system of FIG. 3a in a second connected state, with a sterile connection established.

FIGS. 3a to 3c show a simplified representation of a system 300 for providing a sterile connection between two bodies in a drug delivery system. System 300 can be used for example with injection device 100 and/or injection system 200. FIGS. 3a to 3c show a simplified set of components, to aid the understanding of the reader. FIG. 3a shows the components of the system in an unconnected state. FIG. 3b shows the components of the system in a first connected state in which the components have been moved together for creating a sterile connection. FIG. 3c shows the components of the system in a second connected state, in which sterile connection is formed between the two bodies in the system.

The system 300 for providing a sterile connection can include a first body 310 defining a first volume and a second body 320 defining a second volume. The first and second bodies 310, 320 are shown in an unconnected state in FIG. 3a. The first body 310 can define an opening at one end and a first seal 312 can seal the opening. The first seal 312 can define a first outer sealing surface 314. The second body 320 can define an opening at one end and a second seal 322 can seal the opening. The second seal 322 can define a second outer sealing surface 324. The first body 310 can include a transfer needle 318 that can pierce the first seal 312 and the second seal 322, once the first body 310 and second body 320 are connected, to form a fluid connection between the first and second bodies 310, 320.

There is a risk that if either or both of the first outer sealing surface 314 and the second outer sealing surface 324 are exposed to the environment for an extended period of time that they become contaminated. As described above, in order to ensure that the transfer needle 318 does not become contaminated during this process, due to contamination on either or both of the first outer sealing surface 314 and the second outer sealing surface 324, the first and second outer sealing surfaces 314, 324 can be sterilized at the point at which they are brought into contact.

The system 300 can include a heating element 330 that can sterilize the first and second outer sealing surfaces 314, 324. In embodiments, the heating element 330 can have a strip of electrically or thermally conductive material. The strip may be made of metal, or any other suitable material for transferring electrical energy into heat. The heating element 330 can be shaped to correspond to the shape of the outer sealing surfaces 314, 324 of the first and second seals 312, 322 when brought into a corresponding relationship. The heating element 330 may define substantially parallel opposing planar surfaces, though other configurations are contemplated.

FIG. 3b shows the first body 310 and second body 320 brought into a position where the first seal 312 and second seal 322 are brought into an opposing relationship, i.e., opposite one another, such that the first outer sealing surface 314 and second outer sealing surface 324 are facing each other. In the case where the sealing surfaces 314, 324 are planar, outer sealing surfaces 314, 324 can be located parallel to and facing each other. The heating element 330 can be located between the first body 310 and the second body 320 such that the heating element 330 is in contact with the first and second outer sealing surfaces 314, 324. Once the system has been brought into the position shown in FIG. 3b, the heating element 330 can be heated, for example, through the action of electrical resistance, induction, or in any other suitable way. The heating element 330 thus can transfer heat to the outer sealing surfaces 314, 324 to sterilize the outer sealing surfaces 314, 324.

The heating element 330 can heat the outer sealing surfaces 314, 324 to a predetermined temperature for a predetermined period of time to sterilize the outer sealing surfaces 314, 324. The heating element 330 can be preheated before the system is brought into the position depicted in FIG. 3b such that the time required to sterilize the outer sealing surfaces 314, 324 is minimized and the heat transferred to the first and second seals 312, 322 is minimized. Alternatively, the heating element 330 can be heated only after the system 300 is brought into the position depicted in FIG. 3b. One or more sensors can be applied at any portion of the heating element 330, to monitor the heat transfer between the heating element 330 and the outer sealing surfaces 314, 324. Additionally or alternatively, based on the material properties of the heating element 330 the temperature of the heating element 330 can be inferred from the amount of current provided to the element and the amount of time the heating element 330 is heated. The parameters for determining the threshold temperature and duration of the sterilizing process may be programmed into a control unit, which may automatically operate the heating element 330. To ensure that the outer sealing surfaces 314, 324 are sterilized to appropriate tolerance the temperature of the heating element 330 can remain in excess of 200° C. for 15 seconds or more. In embodiments, the heating element 330 can remain at temperatures significantly greater than 200° C. (e.g., between 250° C. and 300° C. or temperatures greater than 300° C.) for less than 15 seconds.

The heating element 330 can be optimized to minimize the heating time required. For example, the heating element 330 can have a metal with low specific heat capacity—i.e., a material that heats rapidly. As mentioned, the heating element 330 can be pre-heated before being brought into the position in FIG. 3b so that sterilization time, i.e., time in the position of FIG. 3b, is minimized. Optimizing and/or minimizing the sterilization time can reduce or eliminate adverse effects of the heating on medicament that can be contained in one of the first body 310 or second body 320, as can be the case for example with the injection system 200 in FIGS. 2a and 2b.

In embodiments, the second seal 322 can have a heat resistant material, such that it does not transmit heat from the outer sealing surface 324 to the interior of the second body 320. Additionally or alternatively, the second seal 322 can be of a thickness such that heat transfer from the second outer sealing surface 324 to the interior of the second body 320 is minimized or eliminated. Additionally or alternatively, the second seal 322 can have a laminar structure with one or more insulating layers situated between the outer sealing surface 324 and the interior of the second body 320. The insulating layers may have an insulating material that prevents heat transfer from the outer sealing surface 324 to the interior or the second body 320. Additionally or alternatively, the seal 322 can have a multi-part structure where the outer sealing surface 324 covers the opening of the second body 320 to form an air-tight or gas-tight barrier and a stopper seal can ensure that materials within the second body (e.g., medicament) do not escape the interior of the second body 320. Either or both of seals 312, 322, could be formed in the way described above. According to these aspects, materials such as medicament contained within the first body 310 and/or the second body 320 can be protected from adverse effects of the heat treatment applied to the seals 312, 322.

In embodiments, one or both of the first and second bodies 310, 320 can contain a medicament during the sterilization process. However, it is also contemplated that the first and second bodies 310, 320 can undergo the sterilization process described herein prior to filling, i.e., both of the first and second bodies 310, 320 can be empty when sterilized. In such a system, one or both of the first and second bodies 310, 320 can be filled with a medicament after the sterilization process occurs.

The first body 310 and second body 320 can be brought into an opposing relationship, as shown in FIGS. 3b and 3c. In embodiments, a connection assembly 340 that can include co-operating first and second engagement bodies 342, 344 can secure the first body 310 and the second body 320 in the opposing relationship, as shown schematically in FIGS. 3a-3c. The first engagement body 342 and the second engagement body 344 can define corresponding mating components such that the first engagement body 342 and the second engagement body 344 respectively secure the first and second seals 312, 322 opposite each other. For example, the first engagement body 342 and/or the second engagement body 344 can be mechanical structures such as brackets, arms, clamps, holders, or any other structure that can hold the first body 310 and the second body 320 in place. The first and second seals 312, 322 can be secured with a space between the first and second seals 312, 322 and the same can have roughly the same dimensions (e.g., thickness) as the heating element 330. The first and second engagement bodies 342, 344, when secured together, can define a slot 346 through which the heating element 330 can be inserted so as to pass between the seals 312, 322 and arrive at the position shown in FIG. 3b, in which the heating element 330 is in contact with both the first outer sealing surface 314 and second outer sealing surface 324. The heating element 330 can be movable between a first position in which the heating element 330 is not located between the first body 310 and second body 320 (i.e., as shown in FIGS. 3a and 3c) and a second position in which the heating element 330 is located between the first body 310 and second body 320. The heating element 330 may be mounted on a mounting assembly, which is movable between the first and second positions. The mounting assembly may be directly operable by a user or may be controlled by an electronic control unit.

In embodiments, the first and second engagement bodies 342, 344 can be secured when the heating element 330 is located in position between the first and second outer sealing surfaces 314, 324. In this arrangement, opposing forces can be applied to the first and second outer sealing surfaces 314, 324 such that the first and second outer sealing surfaces 314, 324 can be biased towards each other. As a result, a pressure can be applied between the first body 310 and the second body 320. Applying pressure between the first body 310 and second body 320 through the heating element 330 can increase the surface area of the outer sealing surfaces 314, 324 that contacts the heating element 330. For example, an entire surface area of the outer sealing surfaces 314, 324 can contact the heating element 330. Either or both of the seals 312, 322 can have a deformable material, which can further increase the surface area of the outer sealing surfaces 314, 324 that contacts the heating element 330 when the pressure is applied between the first and second bodies 310, 320 ensures that the all points contact is made with the heating element. Pressure can thus be applied to the heating element 330 to secure it in place. Additionally or alternatively, the heating element 330 can be secured in place by other mechanical means such as a clamp, bracket, arms, etc.

Once the heating element 330 has been heated according to the defined parameters relating to temperature and duration, the heating element 330 can be removed from between the first body 310 and the second body 320. The heating element 330 can be removed after a predetermined heating time period has elapsed, the heating element 330 can be removed after a threshold temperature has been reached, and/or surpassed for a predetermined period. One or more temperature sensors can be provided to monitor, for example, the temperature of the heating element 330. The temperature sensors can be a part of the heating element 330 or part of the first and/or second engagement body 342, 344. Removal of the heating element 330 can be controlled by a control unit. For example, the control unit can automatically remove the heating element 330 in response to completion the sanitization process such as when the heating element 330 has been heated to a predetermined temperature for a predetermined period of time, as discussed previously.

In embodiments, the first and second engagement bodies 342, 344 can be biased towards each other and can exert a pressure on the heating element 330. Application of this biasing force can continue while the heating element 330 is being removed, as well as after its removal. When the heating element 330 is removed from the position between the first body 310 and second body 320, this biasing force can cause the first and second bodies 310, 320 to move towards each other as the heating element 330 is removed. That is, the first and second bodies 310, 320 may be biased such that, when the heating element 330 is located between them a pressure is applied to the heating element 330, because the heating element 330 is effectively stopping the first and second bodies 310, 320 from moving to a final position shown in FIG. 3*c*. The biasing force can secure the first body 310 and second body 320 in a connected relationship with the first and second outer sealing surfaces 314, 324 in contact with each other. By bringing the first body 310 and the second body 320 into the connected relationship after sterilization a seal can formed between the outer sealing surfaces 314, 324 through the action of the biasing force simultaneous to the heating element 330 being removed from between the outer sealing surfaces 314, 324. That is, the outer sealing surfaces 314, 324 can come into contact either each other simultaneously with removal of the heating element 330 to seal the outer sealing surfaces 314, 324 from the environment. This seal can provide a reliable aseptic connection between the first seal 312 and second seal 322 and can reduce or eliminate contamination of the first and second sealing surfaces 314, 324 after sterilization. The simultaneous creation of the seal between the first and second sealing surfaces 314, 324 during removal of the heating element 330 can result from elastic expansion of the first and second seals 312, 322 that occurs at the trailing edge of the heating element 330 as it is being removed from between the first and second sealing surfaces 314, 324.

The first body 310 and the second body 320 can remain in the position shown in FIG. 3*c* indefinitely—as long as they are secured together, the seal will remain sterile until the time of use. At the time of use, for example in the case of one of the first body 310 and the second body 320 containing a medicament, a fluid path can be established between the first body 310 and the second body 320. For example, a fluid path may be established by using transfer needle 318 to pierce the first seal 312 and second seal 322.

As described previously, the first and second bodies 310, 320 can be held in place as part of a connection assembly 340. The connection assembly 340 can be a part of a medical device, such as the injection device 100 and injection system 200 shown in FIG. 1 and FIG. 2, respectively. Either of the first body 310 and second body 320 can be an integral part of the medical device. In embodiments, the first body 310 and/or the second body 320 can be inserted and secured into the connection assembly 340. The connection assembly 340 can define a first connection assembly and a second connection assembly. The first connection assembly and second connection assembly can include a corresponding respective first engagement body 342 and second engagement body 344. The connection assembly 340 can be movable from a first position in which the first body 310 and second body 320 are not engaged with each other, or there is clear space between them, as shown in FIG. 3*a*, or below in FIG. 4*a*, to a second position in which the first body 310 and second body 320 are in contact, as shown in FIG. 3*c*. In the embodiment shown in FIGS. 3*a* to 3*c*, the presence of heating element 330 can prevent the first body 310 and second body 320 from moving into contact with one another. The connection assembly 340 can include a latching or locking mechanism which can allow for the first body 310 and second body 320 to be locked in the position shown in FIG. 3*b*. The latching mechanism can provide a biasing force applying pressure between either or both of the first body 310 second body 320, such that when the heating element 330 is removed, the first and/or second bodies 310, 320, can move towards the other to fill the space left by the heating element 330, so as to come into a contact with each other.

In embodiments, the seals 312 and 322 can have a resilient or deformable material that extends beyond an end of the opening of the first body 310 and/or the opening of the second body 320, as shown in FIG. 4*a*. The first seal 312 can extend beyond the first body 310 by a distance a, and the second seal 322 can extend beyond the second body 320 by a distance b. FIG. 4*a* shows the portions of the connection assembly 340 in the same position as the position shown in FIG. 3*a*. The first body 310 and the second body 320 can be brought into a connected position, as shown in FIG. 4*b*. The position shown in FIG. 4*b* can be the same position shown in FIG. 3*b*. The connection assembly 340, which can include the first engagement body 342 and second engagement body 344, can be fixed into a position where the connection assembly 340 holds the first body 310 and the second body 320 such that the ends of the first body 310 and second body 320 are a distance D from each other, as shown in FIG. 4*b*. In embodiments, the distance D can be less than the distance a+b and the first seal 312 and the second seal 322 can deform, as shown by the hatched portion of FIG. 4*b*. That is, the ends of the first and second seals 312, 322 can be compressed by being held in position by the connection assembly 340 when the heating element 330 is disposed between the first and second seals 312, 322.

By holding the first body 310 and the second body 320 the distance D, which can be less than distance a+b, the heating element 330 can be held in place by a positive pressure due to the deformation of the first seal 312 and the second seal 322. The first seal 312 and the second seal 322 can be biased towards each other through a combination of the holding position and the presence of the heating element 330. The heating element 330 can interrupt contact between the first seal 312 and the second seal 322.

As can be seen in FIGS. 4*c* to 4*e*, as the heating element 330 is removed, after having sterilized the first outer sealing surface 314 and second outer sealing surface 324, the first seal 312 and second seal 322 can revert to an undeformed state. In this way, the seal between the first seal 312 and the second seal 322 can form automatically without requiring any movement of the first body 310 and second body 320 towards each other. This is because the position in which the first body 310 and second body 320 are fixed (i.e., the opposing relationship) leads the first seal 312 and second seal 322 to be in contact with each other through the extension of the first seal 312 and second seal 322 out from the first body 310 and second body 320, respectively, by distances a and b. In the configurations shown in FIGS. 4*a* to 4*e*, therefore, the connection assembly 340 may simply fix the first body 310 and second body 320 into their final position, at distance d from each other, and this position the first seal 312 and second seal 323 automatically form a connection when the heating element 330 is not present.

The above-described methods and connection systems can be used with the injection device 100 and/or the injection system 200, discussed above, though the present disclosure is not intended to be limited to such. Moreover, when the methods and connection systems discussed above are used with the injection device 100 sterile connection between the injection device 100 and the medicament container 102 can be achieved. In embodiments, the methods and connections systems described above may be coupled to the septum-end of a medicament container 102 and the connection assembly 340 may be situated within the enclosure in the door 122 of an injection device 100. However, it will be appreciated that the method and connections systems described above may be used to form other sterile connections within a wearable injection device, or it may be used to form connections in other drug delivery systems (e.g. pen type injectors comprising a seal medicament cartridge, infusion pumps, etc.).

Figure 5:
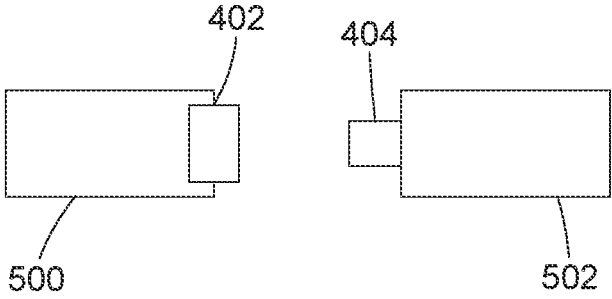
FIG. 5 is a schematic illustration showing a system for filling a medicament container according to an example of the present disclosure.

FIG. 5 shows a container filling system according to the present disclosure. The container filling system can include a first container 500, which can be connected to a first connection assembly 402. The container filling system can include a second container 502, which can be connected to a second connection assembly 404. The first and second connection assemblies 402, 404 can include any of the features discussed above in reference to the connection system 300 and vice versa. The sterilization process described above can be performed between respective surfaces of (or components fluidly attached to) the first container 500 and the second container 502. Accordingly, it is possible to fill the first container 500 or the second container 502 without compromising sterility. The first container 500 can define a vial or cartridge. The second container 502 can be larger, smaller, or the same size as the first container 400. The first container 500 and/or the second container 502 can define a flexible bag or can be a rigid construction.

Figure 6:
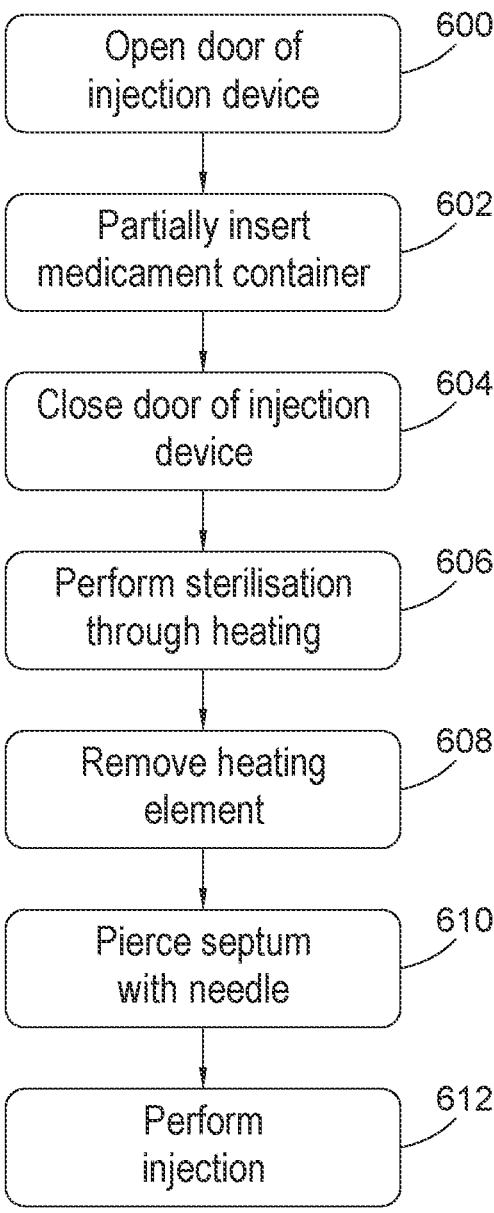
FIG. 6 is a flow chart showing a method of forming an aseptic fluid pathway according to the present disclosure.

FIG. 6 shows a method of forming an aseptic fluid pathway according to the present disclosure. The method of FIG. 6 can be performed using like structures the connection system 300 of FIGS. 3a-3c, the injection device 100, and/or the injection system 200 as described above.

At step 600, a user can open a door of injection device, which can be provided on a patient's body. The injection device can include a second connection assembly. By opening the door, an enclosure in the injection device can be revealed. The enclosure can contain the second connection assembly.

At step 602, the user can select a medicament container that can contain a correct medicament type and dose for a treatment to be administered. The medicament container can include a septum that can seal an opening of the medicament container. The user can couple the injection device with the medicament container by partially inserting the medicament container into the enclosure. The medicament container can be located opposite a second body in the injection device through which the medicament can be delivered to an injection site via a hypodermic needle. This can correspond to the first state illustrated in FIG. 4a. A heating element can be located between a first seal of the medicament container and a second body of the injection device.

At step 604, the user can close the door of the injection device. In so doing, the medicament container can move into a position within the injection device in which the medicament container is ready for a sterile connection between a first outer sealing surface of a seal of the medicament container and a second outer sealing surface of a second body within the injection device. In particular, the closing of the door can bring the medicament container into a biased position in which the first outer sealing surface is in contact with the heating element and the second outer sealing surface is also in contact with the heating element. The closing of the door can move the heating element into position—that is, the movement of the door can be mechanically linked to movement of the heating element between a first position and a second position in which it is in place between the first and second body.

At step 606, the heating element can perform a sterilization procedure by heating the first outer sealing surface and the second outer sealing surface to a predetermined temperature for a predetermined period of time. In embodiments, the closing of the door in step 604 can activate a predetermined heating program to perform the sterilization.

At step 608, the heating element can be removed from between the first outer sealing surface and the second outer sealing surface and can form a sterile connection between the first outer sealing surface and the second outer sealing surface. This can be done through the movement of the first and second body together through a biasing force applied by closing the door of the injection device, which can move the first body towards the second body and can the connection. This can additionally or alternatively be done or through one or more resilient seals reverting to an undeformed state as the heating element is removed.

At step 610, the transfer needle can move through the seal and towards the septum and can ultimately pierce the septum. Once the septum is pierced, a holding mechanism can engage to hold the transfer needle in place. In this state, a fluid pathway between the medicament container and the injection device can be established. This can correspond to the third state illustrated in FIG. 3c.

At step 612, the user can press the button, thereby activating the injection mechanism such that an injection is performed. The medicament can be delivered to the patient through the hypodermic needle.

Other aspects of this disclosure can include a method for creating an aseptic connection in a drug delivery system, a method comprising: providing a first volume comprising a first seal sealing an opening of the first volume, the seal having a first outer sealing surface; providing a second volume comprising a second seal sealing an opening of the second volume, the second seal having a second outer sealing surface; arranging the outer surface of the first seal in an opposing relationship with the outer surface of the second seal; arranging a heating element between the first outer sealing surface and the second outer sealing surface, such that the heating element is in contact with the first outer sealing surface and the second outer sealing surface; applying opposing forces to the first and second outer sealing surfaces, such that the first and second outer sealing surfaces are biased towards each other; heating the heating element to a predetermined temperature for a predetermined period of time to sterilize the first outer sealing surface and second outer sealing surface; and removing the heating element from between the first seal and second seal while continuing to apply the opposing forces to the first and second outer sealing surfaces, such that a seal is simultaneously formed between the first and second outer sealing surfaces.

Because of the provision of the heating element, a simple and time-efficient method for creating an aseptic seal between two bodies is provided. Thus, fluid transfer from the first body to the second body may be performed reliably and with less chance of non-sterile elements from the surfaces of the seals contaminating the flow. Since the seals, and their outer surfaces are brought into an opposing relationship in which they are biased towards each other, i.e. into a position from which they will be joined, the process of simultaneously sterilizing and joining both outer surfaces means that there is almost no opportunity for the seals to become contaminated before the seals are joined together. The predetermined temperature may be a predetermined temperature range, comprising a minimum temperature above which the heating element should be heated, and a maximum temperature which the heating element should not exceed, so as to not damage the sealing surfaces. The time period may comprise one or more time intervals during which the heating element should be at the required temperature, or within the required temperature range.

The heating element may comprise a strip of electrically or thermally conductive material, which may be in the form of a strip, and may be heated by electrical resistance or induction. The strip may be formed so as to be easily removable from between the seals once the sterilization process has taken place.

The first and second outer sealing surfaces may be secured in a contacting relationship once the sterilization process has taken place. The two bodies may then remain in this position indefinitely, or as long as required, without the seal between the first outer sealing surface and second outer sealing surface being compromised.

The first seal may be part of a first connection assembly comprising a first engagement body comprising the first volume, and the second seal may be part of a second connection assembly comprising a second engagement body comprising the second volume. The first engagement body and the second engagement body may comprise corresponding mating components to secure the first and second seals in a contacting relationship.

The first engagement body and second engagement body, when connected to each other, may form a slot though which the heating element extends to contact the first outer sealing surface and second outer sealing surface. The method may further comprise securing the first engagement body and second engagement bodies to each other with the heating element arranged between the first outer sealing surface and second outer sealing surface and removing the heating element through the slot.

This configuration, comprising the connection assembly having first and second engagement bodies, provides for a simple means by which to bring the first and second bodies together and to secure them in position. The slot formed between the first and second engagement bodies, when they are connected together, provides a convenient means by which to insert and/or remove the heating element from the space between the first and second outer sealing surfaces, when the first and second bodies are in position.

The step of removing the heating element from between the first seal and the second seal may take place after the step of securing the first engagement body and second engagement body.

The first seal may seal an enclosure in which a septum of a medicament container is disposed.

The second seal may seal an enclosure in which a tip of a transfer needle is disposed.

The step of arranging the heating element between the first outer sealing surface and second outer sealing surface may comprise inserting the heating element into a space between the first outer sealing surface and second outer sealing surface; and advancing one or both of the first outer sealing surface and second outer sealing surface towards the heating element to a position in which the first outer sealing surface and second outer sealing surface contact the heating element. The first and second outer sealing surfaces may be brought into a fixed position and the heating element then placed between them. Once in this position, the two outer sealing surfaces may be brought into contact with either side of the heating element.

Each of the first and second volumes may be empty during the sterilization process. Alternatively, one of the first and second volumes may contain a medicament during the sterilization process.

In a second aspect there is provided a system for creating an aseptic connection between two components in a drug delivery system, the system comprising a first aseptic volume sealed by a first seal and having a first outer seal surface; a second aseptic volume sealed by a second seal and having a second outer seal surface, and a connection assembly configured to secure the first and second outer seal surfaces in a contacting relationship. The connection assembly comprises a slot through which a heating element is configured to extend to contact the first outer sealing surface and the second outer sealing surface, and a heating element configured to extend through the slot to contact the first and second outer sealing surfaces.

The system described allows for the first and second volumes to be brought together, and an aseptic seal formed between them through the introduction of the heating element.

The preceding detailed description describes systems and methods for ensuring sterility of an on-body injection device. However, the skilled person will understand that the invention is not limited to use in connection with the exemplary on-body device described here. Rather, one or more benefits associated with the present invention may be implemented in connection with other drug delivery devices, or in any case where a sterile connection is to be formed between two bodies having seals which may not be sterile, as will be apparent to the skilled person in light of the preceding detailed description.

The embodiments described and shown in the accompanying drawings above are provided as examples of ways in which the invention may be put into effect and are not intended to be limiting on the scope of the invention. Modifications may be made, and elements may be replaced with functionally and structurally equivalent parts and features of different embodiments may be combined without departing from the disclosure.

What is claimed is:

1. A method for creating an aseptic connection within a medical injection device, the medical injection device comprising a housing configured to receive a medicament container that is sealed with a medicament container seal, a transfer needle sealed within the housing via a housing seal, and a connection assembly that is configured to secure the medicament container within the housing such that the medicament container seal opposes the housing seal, the method comprising:

arranging, via the connection assembly, an outer sealing surface of the medicament container seal in an opposing relationship with an outer sealing surface of the housing seal;

arranging a heating element between the outer sealing surface of the medicament container seal and the outer sealing surface of the housing seal such that the heating element is in contact with the outer sealing surface of the medicament container seal and the outer sealing surface of the housing seal;

applying, via the connection assembly and with the heating element between the outer sealing surface of the medicament container seal and the outer sealing surface of the housing seal, force to at least one of the medicament container or the housing such that the outer sealing surface of the medicament container seal and the outer sealing surface of the housing seal are biased towards each other;

sterilizing, concurrently with applying the force, the outer sealing surface of the medicament container seal and the outer sealing surface of the housing seal by heating, with the heating element, the outer sealing surface of the medicament container seal and the outer sealing surface of the housing seal to a predetermined temperature for a predetermined period of time;

removing the heating element from between the medicament container seal and the housing seal while continuing to apply the force such that the aseptic connection is simultaneously formed between the outer sealing surfaces outer sealing surface of the medicament container seal and the outer sealing surface of the housing seal without breaking the medicament container seal or the housing seal; and fixing, with the connection assembly, the medicament container in a final position that maintains the aseptic connection between the outer sealing surface of the medicament container seal and the outer sealing surface of the housing seal.

2. The method of claim 1, wherein the heating element comprises a strip of electrically conductive material.

3. The method of claim 2, wherein the heating is produced by electrical resistance.

4. The method of claim 1, wherein the heating element comprises a strip of thermally conductive material.

5. The method of claim 4, wherein the heating is produced by induction.

6. The method of claim 1, further comprising securing the outer sealing surface of the medical container seal in a contacting relationship with the outer sealing surface of the housing seal.

7. The method of claim 1, wherein:

applying the force comprises defining a slot between the outer sealing surface of the medical container seal and the outer sealing surface of the housing seal, the method further comprises securing a first engagement body of the connection assembly and a second engagement body of the connection assembly to each other with the heating element arranged in the slot between the outer sealing surface of the medical container seal and the outer sealing surface of the housing seal, and removing the heating element further comprises removing the heating element through the slot.

8. The method of claim 7, wherein removing of the heating element occurs after the securing the first engagement body and the second engagement body.

9. The method of claim 1, wherein the medicament container seal is a septum.

10. The method of claim 1, wherein the housing defines an enclosure, a tip of the transfer needle is disposed within the enclosure, and the housing seal seals the enclosure.

11. The method of claim 1, wherein arranging the heating element comprises:

inserting the heating element into a space between the outer sealing surface of the medical container seal and the outer sealing surface of the housing seal; and advancing at least one of the outer sealing surface of the medical container seal or the outer sealing surface of the housing seal towards the heating element to a position in which the outer sealing surface of the medical container seal and the outer sealing surface of the housing seal each contact the heating element.

12. The method of claim 1, wherein the medicament container is empty.

13. The method of claim 1, wherein the medicament container contains a medicament.

14. The method of claim 1, wherein:

the predetermined temperature exceeds 200° C., and the predetermined period of time is at least 15 seconds.

15. The method of claim 1, wherein fixing the medicament container in the final position further comprises deforming the medicament container seal and the housing seal.

16. The method of claim 1, wherein arranging the heating element between the outer sealing surface of the medical container seal and the outer sealing surface of the housing seal further comprises contacting the heating element with majorities of both the outer sealing surface of the medical container seal and the outer sealing surface of the housing seal.

17. The method of claim 16, wherein arranging the heating element between the outer sealing surface of the medical container seal and the outer sealing surface of the housing seal further comprises contacting the heating element with an entirety of both the outer sealing surface of the medical container seal and the outer sealing surface of the housing seal.

18. The method of claim 1, wherein removing the heating element further comprises withdrawing the heating element in a direction substantially perpendicular to a direction in which the force is applied.

* * * * *